(12) United States Patent
Eum (10) Patent No.: US 8,513,026 B2
(45) Date of Patent: Aug. 20, 2013

(54) TEFLON CONTAINER FOR SAMPLE DECOMPOSITION USING GAS CONDENSATION BY AIR COOLING

(76) Inventor: Young Rok Eum, Gwangmyung (KR)

( * ) Notice: Subject to any disclaimer, the term of this patent is extended or adjusted under 35 U.S.C. 154(b) by 293 days.

(21) Appl. No.: 12/936,517

(22) PCT Filed: Apr. 13, 2009

(86) PCT No.: PCT/KR2009/001873
§ 371 (c)(1),
(2), (4) Date: Oct. 5, 2010

(87) PCT Pub. No.: WO2009/136694
PCT Pub. Date: Nov. 12, 2009

(65) Prior Publication Data
US 2011/0033949 A1 Feb. 10, 2011

(30) Foreign Application Priority Data
May 9, 2008 (KR) ........................ 10-2008-0043664

(51) Int. Cl.
*G01N 1/40* (2006.01)
(52) U.S. Cl.
USPC ........... 436/177; 436/174; 436/181; 422/531; 422/527; 422/549
(58) Field of Classification Search
USPC ................ 422/610, 527, 528, 530, 531, 549, 422/500; 436/174, 177, 181
See application file for complete search history.

(56) References Cited

U.S. PATENT DOCUMENTS

| | | | | |
|---|---|---|---|---|
| 5,022,967 A * | 6/1991 | Stieg | ............................ | 202/197 |
| 6,471,069 B2 | 10/2002 | Lin | | |
| 7,153,477 B2 | 12/2006 | DiCesare | | |

(Continued)

FOREIGN PATENT DOCUMENTS

JP 2000-199760 7/2000

OTHER PUBLICATIONS

Knapp, Guenter. "Mechanized techniques for sample decomposition and element preconcentration." Mikrochimica Acta (1991) 11 445-455.*

Ussing, Hans et al. "A distillation device for small water-samples." Skandinav. Archiv. (1940) 83 169-174.*

(Continued)

*Primary Examiner* — Yelena G Gakh
*Assistant Examiner* — Christopher A Hixson
(74) *Attorney, Agent, or Firm* — Christopher Paul Mitchell (57) ABSTRACT

When an atomic absorption spectrophotometer (AAS) or inductively coupled plasma (ICP) is used, samples must be introduced in a liquid state. Thus, sample decomposition by acids must be performed. Methods for decomposing samples using beakers or microwaves have caused several problems such as loss of volatile elements, excessive use of acids, emission of harmful gases, limitation of sample capacity and amount, and inconvenience of cleaning up. However, the present invention can treat many samples with one acid injection through gas condensation by both heating of a reaction container and air cooling of a collection pipe, wherein the reaction container is made of fluororesin (Teflon) or quartz. Also, if there are many samples, the samples can be treated at once. Furthermore, since the present invention can treat the samples with a conventional heating plate, the invention can be used at inexpensive costs. Additionally, since harmful gases or volatile elements generated in decomposition are condensed in an absorption pipe, anticorrosive effects and accurate data can be obtained. Also, the invention can reduce reagents and prevent both contamination of samples caused by concentration of reagents and air pollution caused by harmful gases generated during decomposition.

7 Claims, 5 Drawing Sheets

(56) References Cited

U.S. PATENT DOCUMENTS

2002/0064484 A1  5/2002  Lin
2002/0131904 A1  9/2002  DiCesare
2003/0053938 A1* 3/2003  Szeles .......................... 422/102

OTHER PUBLICATIONS

International Search Report for PCT/KR2009/001873 mailed Oct. 27, 2009.

* cited by examiner

TEFLON CONTAINER FOR SAMPLE DECOMPOSITION USING GAS CONDENSATION BY AIR COOLING

RELATED APPLICATIONS

This application is a 371 application of International Application No. PCT/KR2009/001873, filed Apr. 13, 2009, which in turn claims priority from Korean Patent Application No. 10-2008-0043664, filed May 9, 2008, both of which are incorporated herein by reference in their entireties.

TECHNICAL FIELD

The present invention relates to a vessel for sample decomposition for decomposing a solid or liquid sample with various kinds of acids in a chemical laboratory, using fluororesin (hereafter, referred to as Teflon). In more detail, the present invention relates to a Teflon vessel for sample decomposition designed to prevent loss of heavy metals volatilized during decomposition, and reduce reagents and decomposition time, by using heat decomposition in a reaction vessel disposed at the lower portion and condensation of a hot gas by air cooling in a collection tube disposed at the upper portion.

BACKGROUND ART

Methods of decomposing sample have used beakers and watch glasses to decompose samples for about hundred years. Although using beakers has the advantage of allowing simple sample decomposition, a large amount of volatile elements, such as mercury and arsenic, are lost through the open upper portion and a large amount of reagents are used by evaporation of the reagents due to heating. Further, the generated harmful gases damage the main body of the heater and reduce the life of the fume hood.

Further, a method has been proposed, which places a cooling tube having a size of 25 cm or more on a round bottom flask of 250 ml, installs an collection tube, and then decomposes a sample with an acid. The cooling tube is a water-cooling type and requires a separate electric chiller. Since the method has a large equipment length, it is difficult to use the equipment on a common hood and to clean the equipment after decomposition. Further, since it can treat at most five samples at one time, it is not suitable to decompose many samples. Further, in terms of technology of the method, the gas evaporating in the reaction vessel condenses and falls down too much, it cannot used for when a large amount of acid requires to evaporate. Therefore, the collection tube has difficulty in achieve the original function due to the water-cooling type cooling tube. That is, most gas evaporating in the reaction vessel falls down in the reaction vessel by the cooling tube, failing to rise to the collection tube, such that there is little relationship between the reaction vessel and the collection tube.

Recently, a method of decomposing a sample using a microwave is commonly used. However, since the microwave performs pressure decomposition, the amount of sample injection is limited. In general, it cannot decompose an inorganic substance of above 0.5 g. Further, the pretreatment of a sample is complicated in the method.

[Document 1] See drawings of pretreatment of zinc and nickel of Korea Soil Test

[Document 2] US EPA Method 3015, 3051, 3052

DISCLOSURE

Technical Problem

The present invention is directed to overcome the problems and it is an object of the present invention to collect harmful gases produced in heat decomposition, prevent loss of volatile elements, reduce minimum use time and decomposition time of reagents for decomposition, and achieve easy conversion into pressure decomposition, by using a Teflon reaction vessel and a collection tube disposed above the vessel. It is another object of the present invention to provide a vessel for sample decomposition for overcoming the problems and a method of decomposing a sample using the vessel.

Technical Solution

In order to accomplish the objects of the present invention, a vessel for sample decomposition includes a reaction vessel 1 having a collection tube connection portion 7 at the upper portion and a collection tube 2, in which the collection tube 2 includes: an intermediate tube 3 having a reaction vessel connection portion 10 at the lower portion to be connected with the upper portion of the reaction vessel 1, an inverse U-shaped tube connection portion 13 and a collection tube cover 16 connection portion on the outer side and the inner side at the upper portion, respectively, and a tube 14 formed to allow a gas produced in the reaction vessel 1 to pass therethrough; an inverse U-shaped tube 4 formed in an inverse U-shape, connected with the inner inverse U-shaped connection portion 13 of the upper portion of the intermediate tube 3, at the lower portion of the inverse U-shape tube, and having predetermined-sized holes 18 above the intermediate tube connection portion 17; and a collection tube cover 5 connected with the outer collection tube cover connection portion 16 at the upper portion of the intermediate tube 3 to cover the inverse U-shaped tube, and a gas outlet 20 allowing gas to pass therethrough at the upper portion. In this configuration, the material of the reaction vessel is any one of Teflon, quartz, and ceramic, and the collection tube 2 is made of Teflon.

Figure 2:
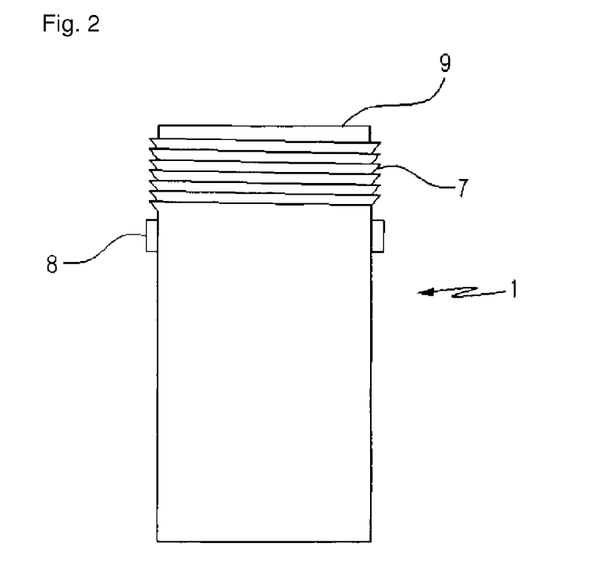
FIG. 2 is a front view of a reaction vessel.
Figure 3:
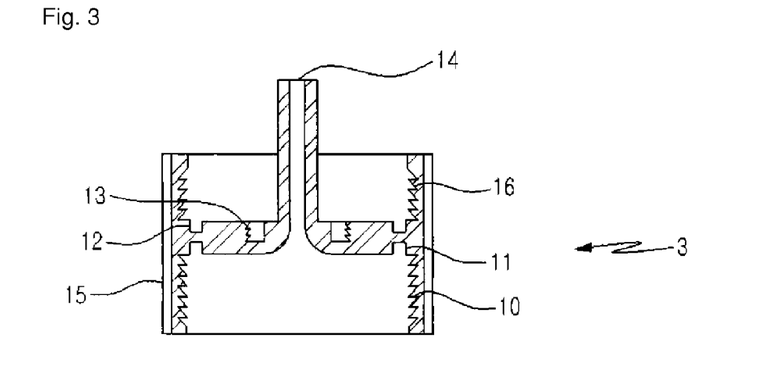
FIG. 3 is a cross-sectional view of an intermediate tube.

The intermediate tube 3 and the reaction vessel 1, the intermediated tube 3 and the inverse U-shaped tube 4, and the intermediate tube 3 and the collection tube cover 5 may be combined by thread-fastening, the reaction vessel 1 has a protrusion 9 extending from the end of the thread, the intermediate tube 3 has a groove 11 formed above the thread to correspond to the protrusion, and an O-ring is inserted between the protrusion 9 and the groove 11 to increase sealing force.

Figure 8:
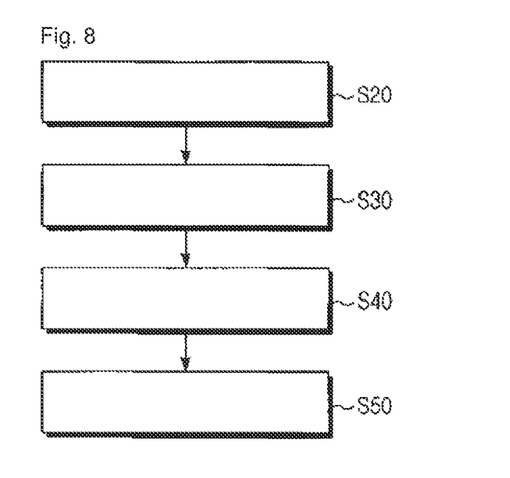
FIG. 8 is a block diagram illustrating a method of decomposing a sample using a vessel for sample decomposition according to the present invention.
Figure 9:
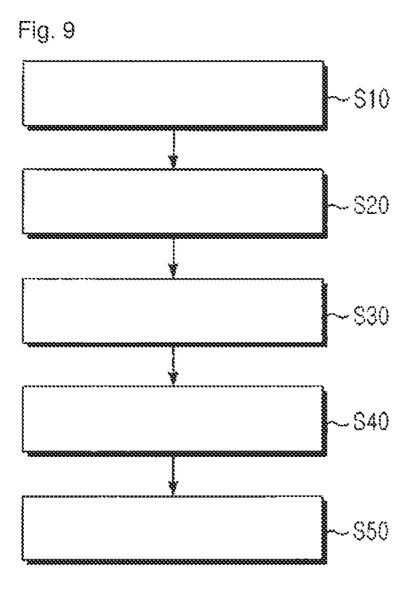
FIG. 9 is a block diagram illustrating a method of decomposing a sample when a sample ashing process is included.

A method of decomposing a sample that uses the vessel for sample decomposition, includes: a sample and sample decomposition solution accommodating step (S20) of putting a sample and sample decomposition solution into the reaction vessel; an absorption solution accommodating step (S30) of combining the reaction vessel with the collection tube and putting absorption solution into the collection tube; a heating step (S40) of heating the vessel for sample decomposition by placing the vessel onto a hot plate; and a sample decomposition step (S50) of decomposing the sample while the sample evaporates in the reaction vessel, moves to the collection tube and is condensed by air-cooling in the collection tube and the condensed solution returns to the reaction vessel by decrease of pressure in the reaction vessel, which are repeated. In sample decomposition using a dry ashing process, the reaction vessel is made of ceramic and a sample ashing step (S10) of ashing the sample by heating the reaction vessel accommodating the sample at 500° C.~600° C. is performed first.

Figure 6:
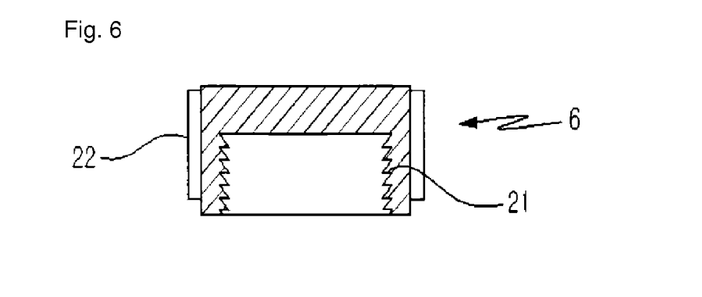
FIG. 6 is a cross-sectional view of a Teflon pressure cover.
Figure 7:
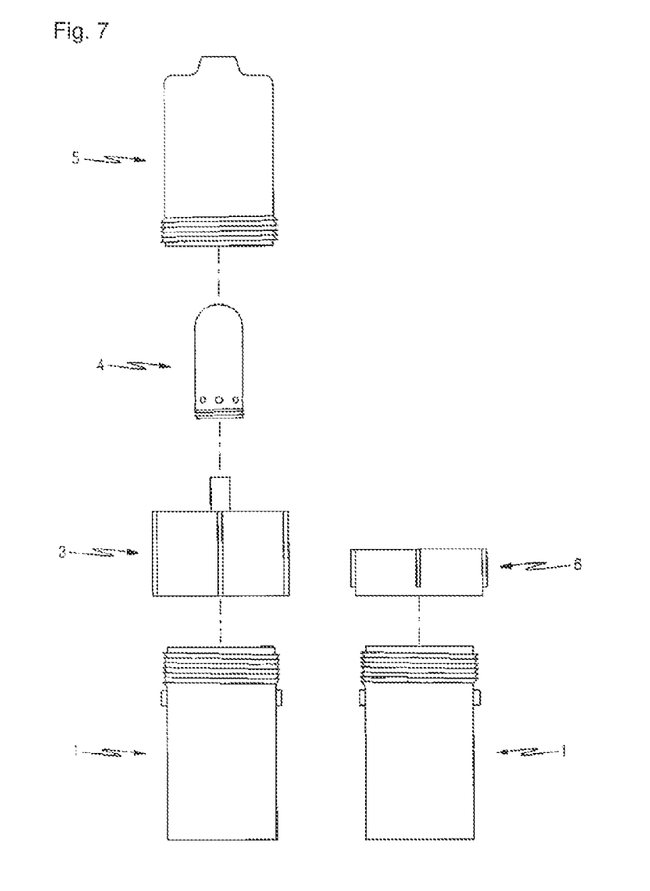
FIG. 7 is a front view showing the entire of a vessel for sample decomposition before assembled and a front view of a vessel for pressure decomposition, according to the present invention.

Further, when pressure decomposition is required, a sample and sample decomposition solution are put into a reaction vessel 1 made of Teflon, and then the sample is pressure-decomposed after closing a Teflon pressure cover 6, instead of the collection tube 2.

advantageous effects

The present invention can use HF (hydrofluoric) acid when the reaction vessel 1 is made of Teflon, and when quartz is selected, decomposition can be achieved by dry ashing <Decomposition by Food Code of KFDA.

Since the amount of necessary reagent with respect to the amount of a sample can be minimized by air-cooling condensation effect of the collection tube in the decomposition, the cost for purchasing the reagent can be reduce. Volatile elements (mercury, arsenic, lead, selenium, tin, and antimony etc.) are collected by the air-cooling condensation effect and the absorption solution (0.5 mole nitric acid or potassium permanganate solution or gold standard solution of 5 ppm of 6 ml to 15 ml) put in the collection tube 2 in advance, such that it is possible to acquire better data without losing the volatile elements. Further, emission of harmful gases is minimized by the air-cooling condensation effect of the collection tube 2, such that it is possible to corrosion of the fume hood or the hot plate body, thereby extending the life of the device. Furthermore, it is possible to expect to prevent air pollution due to emission of the harmful gases produced in decomposing NOx, Cox, SOx etc.

It is possible to covert the decomposition into pressure decomposition by easily replacing the collection tube 2 with the Teflon pressure cover 6. The reaction vessel 1 made of Teflon and the pressure cover 6 according to the present invention can be used for the sample decomposition method of submarine deposits proposed from Korea <ocean environmental pollution process examination method>.

In a practical analysis, since excessive acid remaining in the solution, which has been decomposed, after decomposition has an adverse effect on the analysis device or analysis result (corrosion of the analysis device and prevention of mattress), when the excessive acid remaining in the decomposed solution is heat-evaporated, as described in detail in the disclosure, it is possible to reduce waste of electric energy and air pollution and prevent corrosion of the hot plate and the fume hood.

When the present invention is applied to the pretreatment process of zinc and nickel which is proposed from Korea <Soil pollution official examination method>, it is possible to process a large amount of sample at once and ensure a space in a laboratory in comparison with the existing methods. That is, according to the present invention, it is possible to perform decomposition by sticking an exclusive hot block or using a hot plate commonly used in laboratories; therefore, the present invention can be widely used in chemical laboratories at low cost. In particular, it can be expected to suppress import of expensive foreign devices for analyzing a sample.

Finally, the Teflon vessel is higher in use temperature than common plastic (continuous use temperature of Teflon is 260° C.), strong against acid, and difficult to break as compared with a glass vessel, such that it is not easily disused and environmental pollution due to wastes.

MODE FOR INVENTION

The present invention can use Teflon, quartz, and ceramic first to select a material of a reaction vessel 1. Although various kinds of Teflon may be selected, it is preferable to select PFA (Perfluoro alkoxy) that can be injection-molded. Injection molding is to melt raw Teflon with heat and form it with a mold, which produces smooth surface as compared with extrusion molding, such that a small amount of heavy metal, such as mercury, is adsorbed in the vessel and cleaning after decomposition is very easy.

In decomposed in a dry ashing process, quartz can be used at higher temperature than the Teflon when ashed at high temperature of 500° C. to 600° C., such that a reaction vessel can be made of quartz, which can be used as a decomposition vessel.

Figure 1:
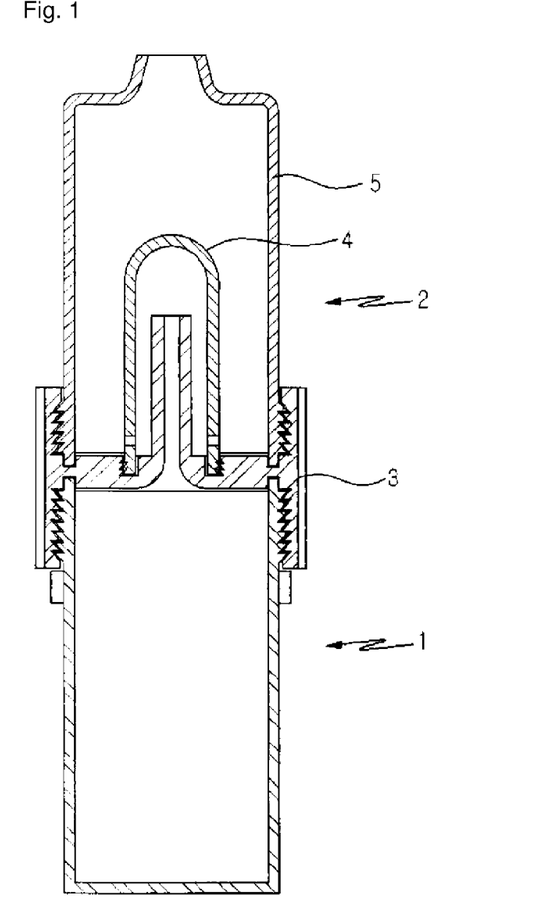
FIG. 1 is a cross-sectional view showing the entire of an assembled vessel for sample decomposition according to the present invention.

A vessel for sample decomposition according to the present invention includes a reaction vessel 1 and a collection tube 2 disposed thereon. The collection tube 2 is composed of an intermediate tube 3, an inverse U-shaped tube 4, and an collection tube cover 5.

The intermediate tube 3 is connected with the reaction vessel 1 thereunder, and the inverse U-shaped tube 4 and the collection tube cover 5 thereon. The intermediate tube and the reaction vessel can be combined in various ways. In various ways, it is preferable to select thread-fastening to prevent leakage of water and leakage of gas under some reaction pressure generated in decomposition. It can be designed to endure high reaction pressure in the reaction vessel very well, by selecting screw-fastening as the thread-fastening. Further, it is possible to prevent leakage of water and maintain high sealing force by inserting a separate O-ring into the joint. The intermediate tube 3 and the inverse U-shaped tube 4 can be selective combined by the various ways, but it is preferable to select thread-fastening. In this case, it is required to prevent leakage of water, it is possible to prevent leakage of water by inserting an O-ring first before inserting the inverse U-shape tube 4. The collection tube cover 5 connected with the intermediate tube 3 is also fastened by thread-fastening, in which they are completed sealed by forming a groove 12 where the intermediate tube 3 is combined and turning and fitting it. If water is likely to leak, the O-ring is inserted first, before the combination.

The intermediate tube 3 has a tube 14 having an inner diameter of 2 mm to 20 mm and a length of 10 mm to 100 mm, such that it prevents backward flow of condensed liquid or allow an evaporating gas to smoothly flow into the collection tube 2. Further, prominences and depressions are formed on the outer surface of the intermediate tube 3 to prevent slip on the hand when combining with or separating from the reaction vessel 1 or the collection tube 5.

Figure 4:
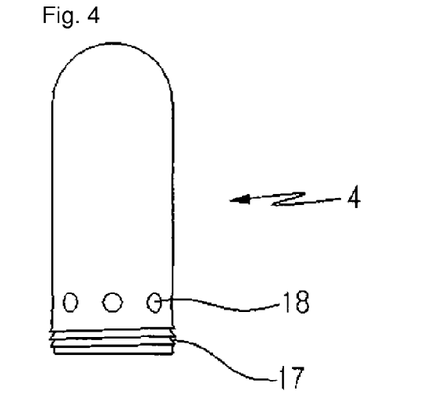
FIG. 4 is a front view of an inverse U-shaped tube.

Two to ten holes 18 having an inner diameter of 1 mm to 5 mm are formed at the lower portion (right above the thread) of the inverse U-shaped tube 4 to induce discharge of evaporating gas. A hot gas coming out through the holes 18 is condensed by the air outside the collection tube 2 and helps volatile elements to be adsorbed while meeting the existing absorption solution (0.5 mole nitric acid or potassium permanganate solution or gold standard solution of 5 ppm of 6 ml to 15 ml).

Figure 5:
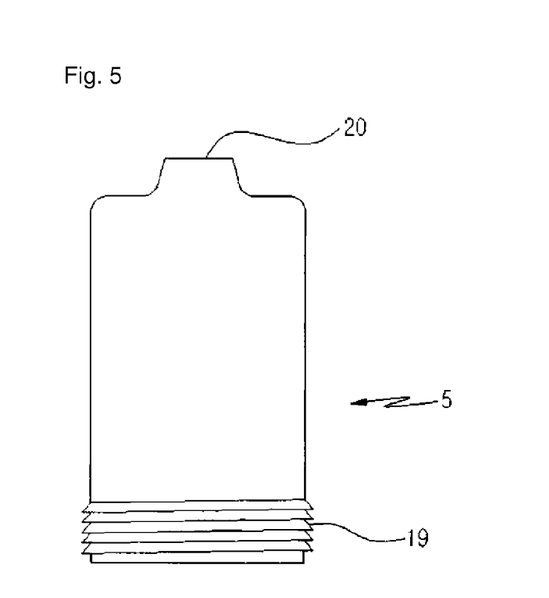
FIG. 5 is a front view of a collection tube cover.

A gas outlet 20 having an inner diameter of 2 mm to 20 mm is formed at the upper portion of the collection tube cover 5 to induce discharge of an evaporating gas. Absorption solution (0.5 mole nitric acid or potassium permanganate solution or gold standard solution of 5 ppm of 6 ml to 15 ml) can be inserted into the collection tube 2 through the gas outlet 20 by a pipet to collect mercury (Hg), which is a volatile element. Further, the gas outlet 20 allows the solution condensed by air after decomposition or the absorption solution to be discharged.

The parts of the present invention were designed such that pollutants do not adhere therein, by accurately surface-finishing in the molding such that the surface is maximally made smooth.

In the use of the present invention, the Teflon decomposition vessel formed by combining the reaction vessel 1 with the collection tube 2 is heat-decomposed by a hot plate of a hot block. When the sample is an organic substance, the sample of maximum 2 g to 3 g can be decomposed under an assumption that the sample is dry, and a single acid or a mixed acid is selected in accordance with the properties of the sample and then the selected acid of about 20 ml to 25 ml is put in with the sample. As the heat decomposition starts, unlike the decomposition method using a beaker, gas is condensed by air in the collection tube 2 at the upper portion, while, in the reaction vessel 1, reaction pressure is decreased by evaporation of the reagent and the condensed liquid drops from the collection tube 2 into the reaction vessel 1 again, such that complete decomposition can be achieved only by the initially injected reagent.

In setting the decomposition temperature, the temperature is maintained for about 20 to 40 minutes when harmful gases, such as NOx and COx, starts to be produced at about 80° C. to 90° C., and then it can be freely set in accordance with the properties of the sample. The reason that the decomposition slows starts at low temperature is to prevent rapid increase of the reaction pressure generated by rapid heating at high temperature. The reaction vessel 1 and the intermediate tube 3 can be combined by screw-fastening to endure the reaction pressure, and at the same time, the reaction vessel 1 and the intermediate tube 3 were designed to be turned and fitted such that the protrusion 9 right above the collection tube connection portion 7 of the reaction vessel 1 is fully fitted in the groove 11 at the lower portion of the intermediate tube, thereby achieving complete sealing. If they are combined by common fitting, they cannot endure the reaction pressure and the gas is likely to leak, or the reaction vessel 1 and the intermediate tube 3 are likely to separate or explode.

Accurate temperature control is required in setting temperature because the volatile elements are very sensitive to temperature. When the reaction vessel 1 is heated at about 200° C. to 250° C., the temperature of the collection tube 2 is measured at about 50° C. to 70° C. This is because the air-cooling outside the collection tube 2 prevents temperature from increasing. Mercury (Hg) volatilizes at 90° C. and arsenic compound (AsCl) volatilizes at 130° C., such that the air-cooling outside the collection tube plays a large role.

Further, the reagent is evaporated and condensed by heating the reaction vessel 1 and air-cooling the collection tube 2, in which when the reagent completely evaporates, the reaction pressure inside the reaction vessel 1 decreases. Accordingly, the liquid condensed in the collection tube 2 drops down again into the reaction vessel 1 and functions as a reagent again for sample decomposition. It is required to injection more reagent in common beakers, but it is not required to additionally injection a reagent in the present invention. This makes it possible to expect to prevent the sample from being polluted by condensation of reagent when excessive reagents are used, and save the management cost of the laboratory.

In accordance with the user's purpose, it may be intended to evaporate excessive acid during the decomposition. In this case, it is possible to prevent consumption of electric energy during the heat evaporation process, such as common beakers, and corrosion of the hot plate and damage to the fume hood due to emission of harmful gases, by sealing the gas outlet 20 of the collection tube cover 5 and separating the reaction vessel 1 from the collection tube 2 to discharge the condensed liquid in the collection tube 2 to a waste tub through the gas outlet 20.

It is possible to perfume decomposition under lower pressure of about 75 psi, by replacing the reaction vessel 1 and the collection tube 2 with the Teflon pressure cover 6. Similarly, in this case, the cover is designed to endure the reaction pressure generated in reaction by forming a groove for thread-fastening. Further, since pressure decomposition is performed, prominences and depressions 22 are formed at the grip to make opening and closing easy.

In flow of the gas produced in the decomposition in the present invention, first, the hot gas produced in the reaction vessel 1 passes through the holes 18 at the lower portion of the inverse U-shaped tube 4 through the tube 14 of the intermediate tube 3 and is collected while passing through the absorption solution (0.5 mole nitric acid or potassium permanganate solution or gold standard solution of 5 ppm of 6 ml to 15 ml) at the same time, and the start to be cooled (the hot gas passes through the absorption solution while producing air bubbles due to the reaction pressure and production of gases). The gas passing through the absorption solution is changed in temperature by the air-cooling applied at the outside of the collection tube cover 5, and the remaining gas flows outside through the gas outlet 20 of the collection tube cover 5.

As described above, in the present invention, the gas flow is performed in a closed type, which does not use the Teflon pressure cover 6. Therefore, when a sample contains a small amount of elements and a large amount of sample is required in decomposition, it is possible to decompose the sample by maximum 2 g to 3 g, by using the vessel for sample decomposition and the method of decomposing a sample according to the present invention.

In the present invention, a sample of about 0.5~3 g is put into the Teflon reaction vessel 1, and then a predetermined amount of nitric acid, hydrochloric acid, sulfuric acid, perchrolic acid, hydrogen peroxide, hydrofluoric acid, and phosphoric acid, or a mixture of them is put. Thereafter, absorption solution (distilled water, dilute nitric acid, potassium permanganate solution, or gold standard solution of 5 ppm of about 15 ml) is put into the collection tube 2 composed of the intermediate tube 3, the inverse U-shaped tube 4, and the collection tube cover 5 through the gas outlet 20 of the collection tube cover 5 by a laboratory pipet, in accordance with the user's selection. Further, the reaction vessel 1 and the collection tube 2 are combined and then heating is started by placing the hot plate thereon or a sticking a hot block. In general, it is possible to reduce the decomposition time, by using a block type exclusive heater rather than a hot plate type heater. The decomposition temperature may be adjusted in accordance with the kinds of sample and the decomposition standard of the inside and outside of the country for decomposition.

In water sample decomposition proposed by <Korea standard methods for the examination of water> or <USEPA>, acid decomposition is performed after temperature is set around 90° C.~140° C.

<Food Code> proposes a dry asking process; therefore, the sample is ashed at high temperature and finished with nitric acid in a quartz reaction vessel instead of the Teflon reaction vessel 1.

When the sample is soil, the present invention can be applied by liquation of 1 mole hydrochloric acid and a pretreatment method of nickel, zinc, mercury, and arsenic, which is proposed in Korea <Soil pollution official examination method>. Nickel and zinc are analyzed in two hours after putting 0.5 mole dilute nitric acid of 15 ml into the collection tube 2 and slowly heating it by about 80° C.~180° C. (some droplets of nitric acid is injected when bubbles are produced, for organic substance-rich soil (containing organic substances of above 10%), particularly the soil of JejuDo. In this process, the solution in the collection tube 2 drops into the reaction vessel by itself with the decrease of the reaction pressure due to cooling of the reaction vessel 1, and the decomposed liquid collected in the reaction vessel 1 is used as analysis solution. As for mercury, decomposition is performed after putting potassium permanganate solution of about 6 ml to 15 ml into the reaction vessel and the collection tube.

Submarine deposits or ocean wastes proposed from <ocean environmental pollution process examination method> are decomposed with nitric acid for 40 minutes and then pressure-decomposed with the cover closed, using the Teflon pressure cover 6 instead of the collection tube 2.

When excessive acid is evaporated in sample evaporation, it is possible to directly discharge the condensed liquid collected in the collection tube 2 by closing the gas outlet of the collection tube cover 5 first and the separating the reaction vessel 1 from the collection tube 2. In this process, rapid evaporation can be achieved by setting temperature to about 230° C.~260° C. in the evaporation.

According to the present invention, the four assemblies are disassembled and cleaned with a neutral detergent and then cleaned with acid in solution having a distilled water:nitric acid:hydrochloric acid ratio of 8:1:1.

At least supersonic cleaning should not used, and the acid cleaning should be necessarily included. The reason that the parts are cleaned with nitric acid and hydrochloric acid is that the degree of acid cleaning (liquation) is different for each element. It is required to prevent the parts from being contaminated in drying with a drier after the cleaning. The four assemblies should be stored in a close space after the drying.

The invention claimed is:
1. A vessel for sample decomposition, comprising;
   a reaction vessel having a connection portion to be combined with a collection tube thereon; and
   the collection tube composed of an intermediate tube, an inverse U-shape tube, and a collection tube cover,
   wherein the intermediate tube has a reaction vessel connection portion at the lower portion to be connected with the upper portion of the reaction vessel, an inverse U-shaped tube connection portion and a collection tube cover connection portion on the outer side and the inner side at the upper portion, respectively, and a tube formed to allow a gas produced in the reaction vessel to flow to the inverse U-shaped tube,
   the inverse U-shaped tube has an intermediate tube connection portion to be connected with the inverse U-shaped connection portion of the intermediate tube, at the lower portion, to be combined in an inverse U-shape,
   predetermined-sized holes are formed above the intermediate tube connection portion,
   the collection tube cover is combined with the intermediate tube by the collection tube cover connection portion to cover the inverse U-shaped tube, and
   a gas outlet is formed at the upper portion of the collection tube cover to allow air to pass therethrough.

2. The vessel for sample decomposition according to claim 1, wherein the material of the reaction vessel is any one of Teflon, quartz, and ceramic, and
   the collection tube is made of Teflon.

3. The vessel for sample decomposition according to claim 1, wherein the intermediate tube and the reaction vessel, the intermediated tube and the inverse U-shaped tube, and the intermediate tube and the collection tube cover are combined by thread-fastening.

4. The vessel for sample decomposition according to claim 3, wherein the reaction vessel has a protrusion extending from the end of the collection tube connection portion,
   the intermediate tube has a groove formed above the thread to correspond to the protrusion, and
   an O-ring is inserted between the protrusion and the groove to increase sealing force.

5. A method of decomposing a sample that uses the vessel for sample decomposition, the method comprising:
   providing the vessel of claim 1;
   a sample and sample decomposition solution accommodating step of putting a sample and sample decomposition solution into the reaction vessel;
   an absorption solution accommodating step of combining the reaction vessel with the collection tube and putting absorption solution into the collection tube;
   a heating step of heating the vessel for sample decomposition by placing the vessel onto a hot plate; and
   a sample, decomposition step of decomposing the sample while the sample evaporates in the reaction vessel, moves to the collection tube and is condensed by air-cooling in the collection tube and the condensed solution returns to the reaction vessel by decrease of pressure in the reaction vessel, which are repeated.

6. The method of decomposing a sample according to claim 5, wherein the reaction vessel is made of ceramic,
   asking the sample by heating the reaction vessel accommodating the sample at 500 C~600 C is performed first.

7. The vessel for sample decomposition according to claim 2, wherein the intermediate tube and the reaction vessel, the intermediated tube and the inverse U-shaped tube, and the intermediate tube and the collection tube cover are combined by thread-fastening.

* * * * *